United States Patent [19]

Nerli

[11] Patent Number: 5,197,875
[45] Date of Patent: Mar. 30, 1993

[54] DENTAL SYRINGE COVERS

[76] Inventor: Robert A. Nerli, 15 El Quanito Way, Burlingame, Calif. 94010

[21] Appl. No.: 806,481

[22] Filed: Dec. 13, 1991

Related U.S. Application Data

[63] Continuation-in-part of Ser. No. 667,422, Mar. 11, 1991, abandoned, which is a continuation of Ser. No. 373,507, Jun. 30, 1989, Pat. No. 4,998,880, which is a continuation-in-part of Ser. No. 118,170, Nov. 9, 1987, Pat. No. 4,859,182.

[51] Int. Cl.⁵ ........................ A61G 17/02; A61C 1/16
[52] U.S. Cl. ........................................ 433/80; 433/116
[58] Field of Search ................... 433/80, 84, 91, 96, 433/116; 604/73, 77, 247

[56] References Cited

U.S. PATENT DOCUMENTS

| | | | |
|---|---|---|---|
| 3,401,691 | 9/1968 | Beu | 433/80 |
| 3,794,091 | 2/1974 | Ersek et al. | 128/6 |
| 4,859,182 | 8/1989 | Nerli | 433/80 |
| 4,907,968 | 3/1990 | Eisner et al. | 433/80 |
| 4,998,880 | 3/1991 | Nerli | 433/80 |
| 5,049,071 | 9/1991 | Davis et al. | 433/80 |
| 5,059,172 | 10/1991 | Sutherland et al. | 604/73 |

Primary Examiner—Robert P. Swiatek
Assistant Examiner—Cindy A. Cherichetti
Attorney, Agent, or Firm—Thomas M. Freiburger

[57] ABSTRACT

Dental syringe covers are described in several different forms. In one form the syringe cover is of a soft, rubbery material at least at its tip, the tip being formed into a one-way valve by a duckbill construction so that fluid cannot enter from outside. In all embodiments the syringe cover, tapered in shape, fits tightly over the metal dental syringe so that no liquid from the syringe can flow backward over the surface of the syringe. Another feature is a longitudinal gap between the syringe tip and the tip of the syringe cover. The gap functions to isolate the syringe tip from the exterior environment as well as to improve the stream of air, water or air/water mix delivered from the syringe. Preferably the syringe covers include an enlarged generally bell-shaped feature at the end opposite the tip, providing a surrounding cover or sheath for a nut or other fastener typically present at the base end of the metal syringe. This enlarged end surrounds the nut but generally makes little contact with the nut, and in some embodiments provides a handle for gripping the syringe cover to install it over the syringe. The syringe covers of the invention are inexpensive and preferably disposable, but may be sterilizable.

18 Claims, 5 Drawing Sheets

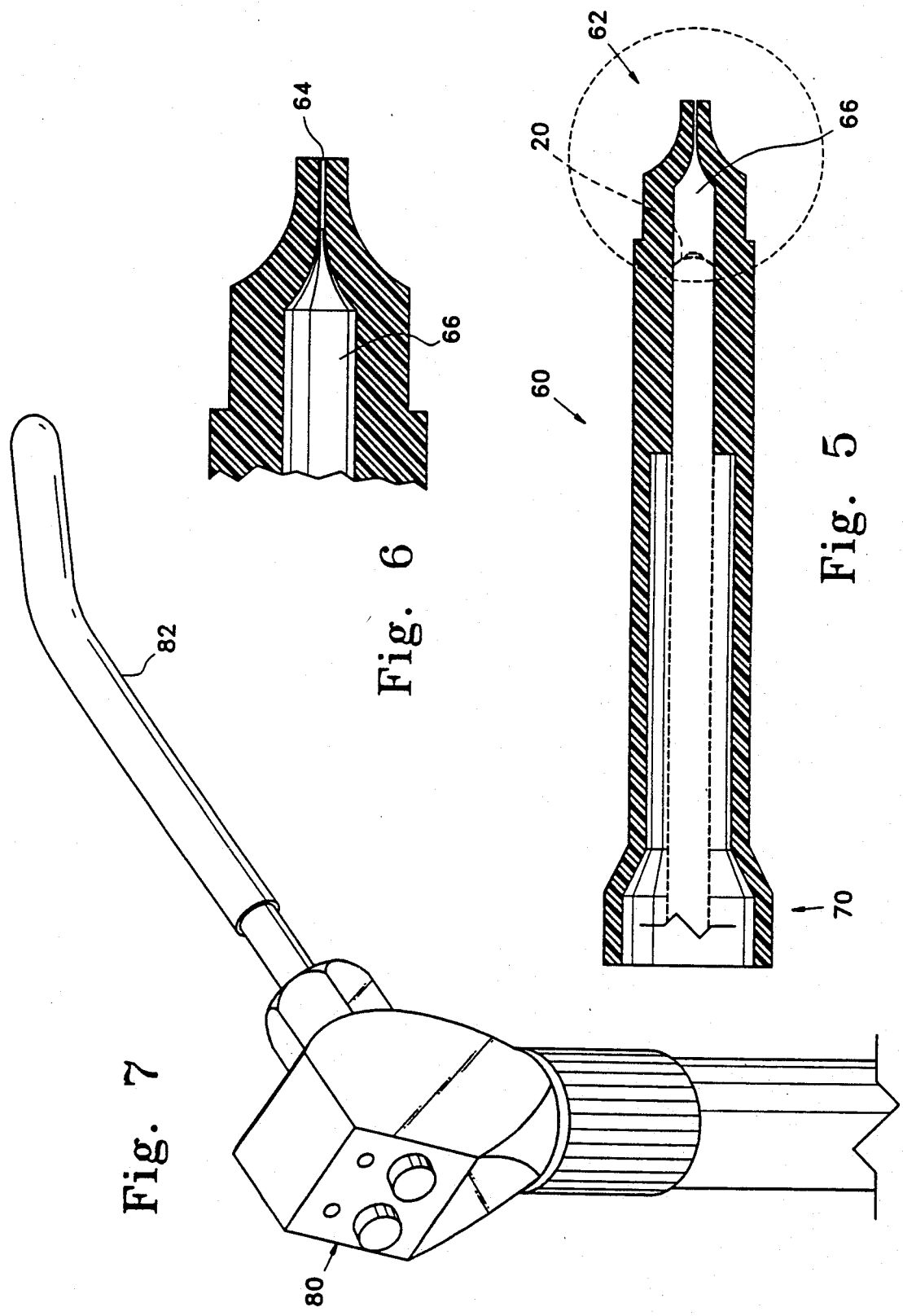

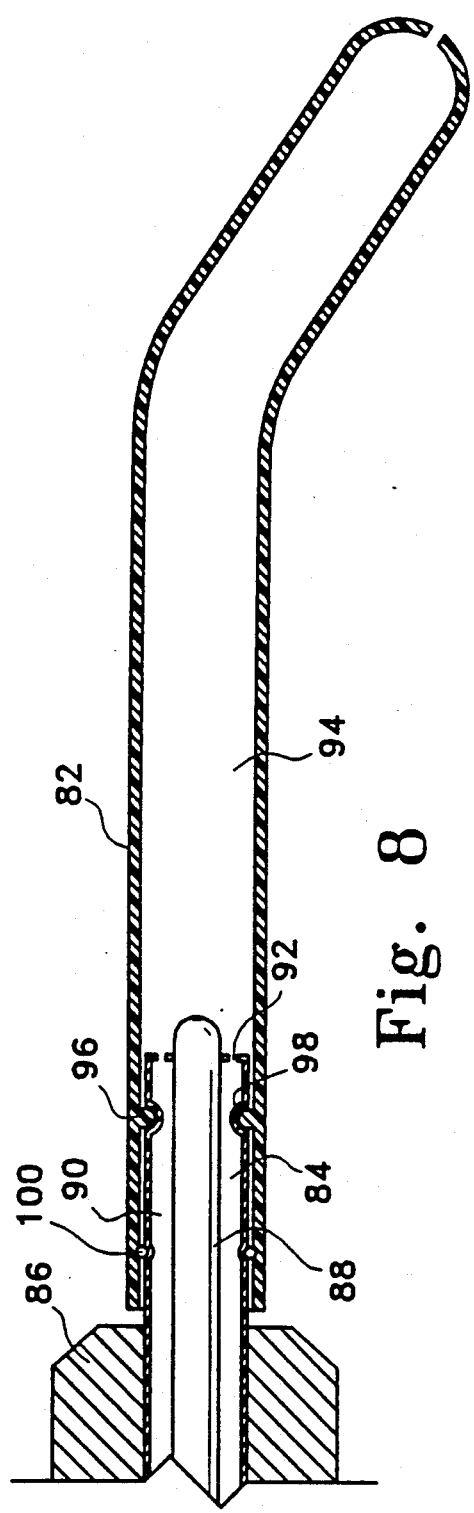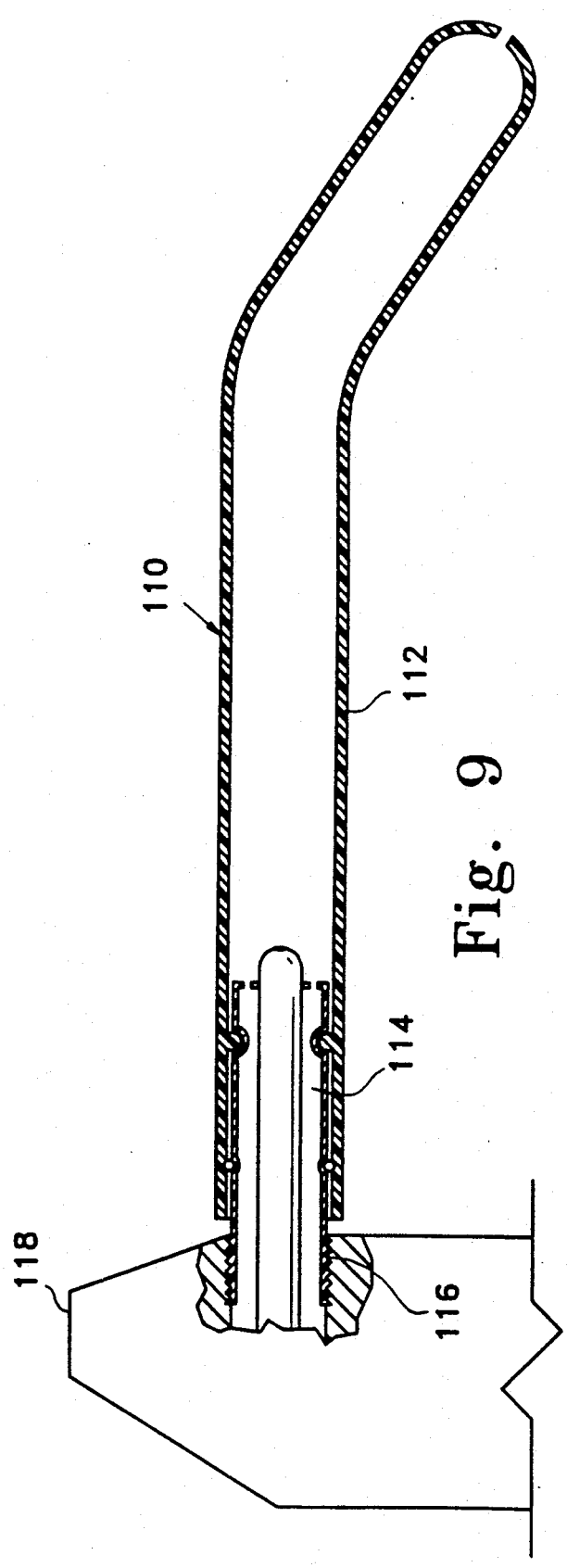

DENTAL SYRINGE COVERS

REFERENCE TO RELATED APPLICATIONS

This application is a continuation in part of application Ser. No. 667,422, filed Mar. 11, 1991, now abandoned, which was a continuation of application Ser. No. 373,507, filed Jun. 30, 1989, now U.S. Pat. No. 4,998,880, which in turn was a continuation in part of application Ser. No. 118,170, filed Nov. 9, 1987, now U S. Pat. No. 4,859,182.

BACKGROUND OF THE INVENTION

The invention relates generally to prevention of communication of infectious diseases. More specifically, the invention is concerned with a hygienic device for covering a dental syringe to prevent cross contamination via the syringe from one patient to a succeeding patient.

Dental syringe covers have been known, in several forms. Nerli U.S. Pat. No. 4,859,182 (referenced above) describes a safety sheath for a dental syringe comprising generally a cylindrical tubular sleeve having an aperture at its tip, which may have a flap-type valve for closing the aperture. The device covered the cylindrical, needle-like portion of the dental syringe, but not the nut-like fastener at the base of the syringe, which secures the syringe to a larger handle portion.

Nerli U.S. Pat. No. 4,998,880 (also referenced above) discloses additional configurations of dental syringe cover devices or sheaths for preventing contamination. The patent describes a nut cover at a base end of the syringe cover, extending over the nut or threaded fastener of the dental syringe itself. Also disclosed (see FIG. 6) is an air gap between the tip of the dental syringe and the end of the syringe cover, which further isolates the dental syringe nozzle from the surrounding environment. The patent further discloses a replaceable, disposable dental syringe beak in lieu of a beak cover. U.S. Pat. No. 4,998,880 is incorporated herein by reference.

Eisner U.S. Pat. No. 4,907,968 disclosed another dental syringe covering shield which had an enlarged nut cover at its base end, also with a further backsplash collar shield at the end of the nut cover. The nut cover was emphasized as fitting with close contact over the nut.

The present invention includes some of the features of the Nerli patents referenced above, as well as additional features which greatly enhance the effectiveness, convenience of use and contamination prevention ability of a prophylactic dental syringe cover.

SUMMARY OF THE INVENTION

A dental syringe cover according to the present invention has features which add security against cross contamination as well as features which enable the user to more conveniently and quickly install the syringe cover over a dental syringe. The syringe cover preferably is disposable, but may be capable of autoclaving for re-use.

At the liquid delivery end of the syringe cover, there preferably is included a gap or space near the tip, beyond the point to which the dental syringe will extend. This provides an internal cavity, beyond the tip of the dental syringe, which will normally contain some liquid but which will isolate the dental syringe tip from the environment. The gap or chamber, by containing liquid during operation of the syringe, allows the nozzle opening to form a proper stream of fluid exiting the syringe cover.

At the opposite end of the syringe cover is preferably included an enlarged, bell-shaped feature which not only covers the nut or fastener of the dental syringe, but also can act as a type of handle for gripping by the user. In particular, the enlarged end enables the user conveniently to rotate the metal syringe and cover to achieve different angles of the tip without having to use two hands. The enlarged end does not grip the nut and in fact preferably does not contact the side facets of the nut, allowing the syringe and cover to be rotated relative to the nut.

Another important feature of the invention is a tight fit between the dental syringe and the syringe cover shank. This prevents contaminating liquids from flowing back over the surface of the dental syringe, between the syringe and the cover. The tight fit may be via tapering of the syringe cover, to a portion having a slightly smaller inside diameter than the outside diameter of the dental syringe, effecting a seal between the two surfaces; or it may be via an internal sleeve of smaller diameter fitted into the syringe cover near its tip, this sleeve having a tapered inner surface which must be force-fitted over the tip of the dental syringe to accomplish the liquid seal.

In one specific embodiment of the invention, the syringe cover may have a valve at its nozzle end, in the form of a duckbill or slit-type valve formed in a soft, rubbery material. This embodiment of the syringe cover may be essentially integral throughout its length, but in one preferred embodiment with a greater hardness and rigidity at the enlarged end than at the tip. This enables the duckbill valve to function effectively and reliably with softer material, while a considerable portion of the syringe cover toward the enlarged end is more rigid so as to tightly grip against the dental syringe. The cover is thereby prevented from expanding in use and blowing off.

In another embodiment, which may be formed of polyethylene or polypropylene, the enlarged nut cover end has a series of radial projections or embossings which are conveniently gripped between the fingers of a user for installation.

In a further embodiment of the invention, a disposable syringe tip is provided which eliminates the need for any cover.

It is therefore among the objects of the invention to improve the effectiveness, efficiency and reliability of dental syringe covers in preventing cross-contamination between dental patients. These and other objects, advantages and features of the invention will be apparent from the following description of preferred embodiments, considered along with the accompanying drawings.

DESCRIPTION OF THE DRAWINGS

FIG. 5 is a side elevational section view showing another embodiment of the invention, including a duckbill type valve at the outlet end of the syringe cover.

FIG. 6 is a detail view showing the duckbill valve of the embodiment of FIG. 5.

FIG. 7 is a perspective view showing a dental syringe with a snap on disposable tip.

FIG. 8 is a sectional view showing the disposable tip of FIG. 7.

FIG. 9 is view showing a disposable syringe beak in accordance with another embodiment of the invention.

DESCRIPTION OF PREFERRED EMBODIMENTS

Figure 1:
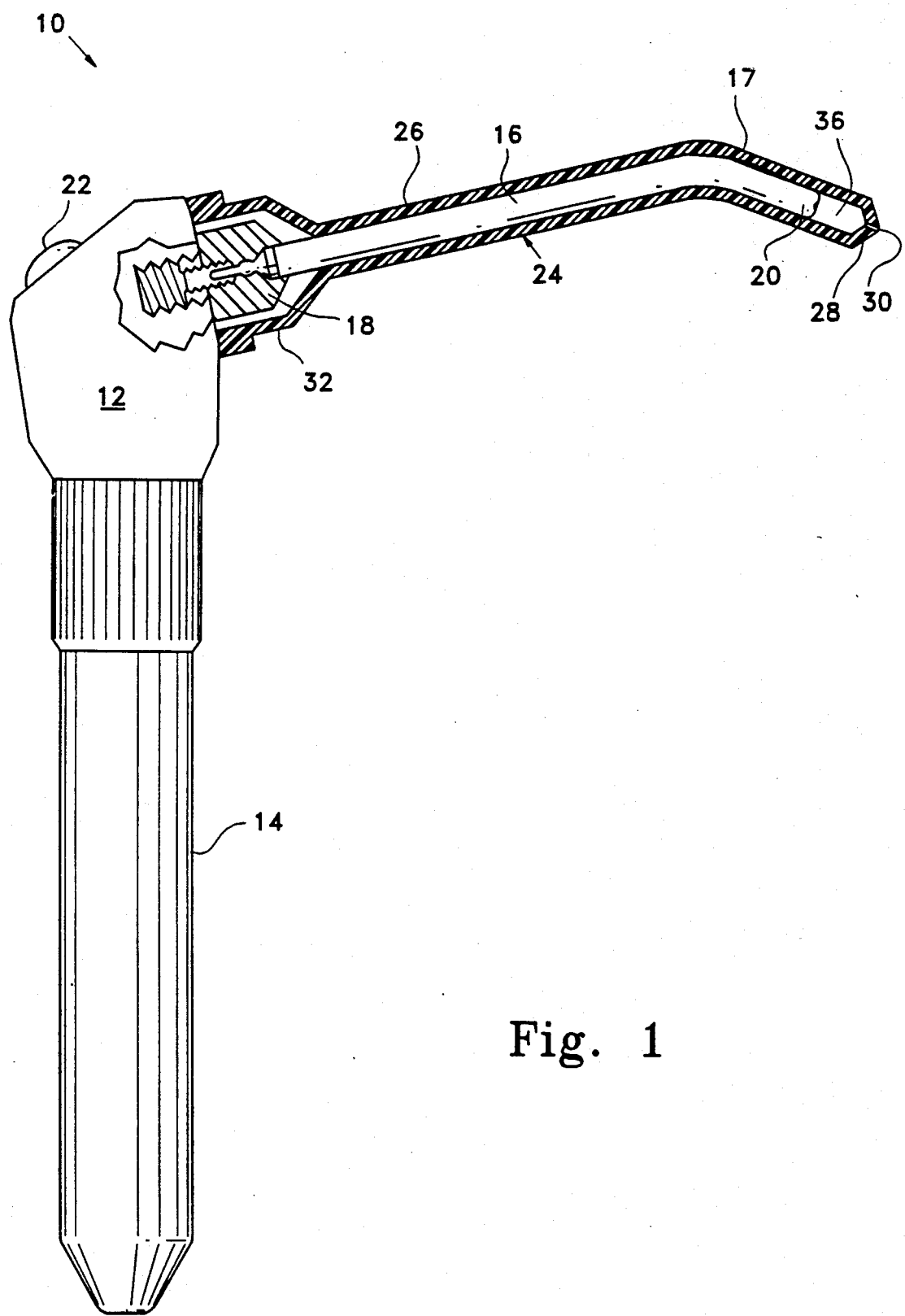
FIG. 1 is a side elevation view partially in section, showing a dental syringe with a syringe cover or sheath in accordance with the invention.
Figure 2:
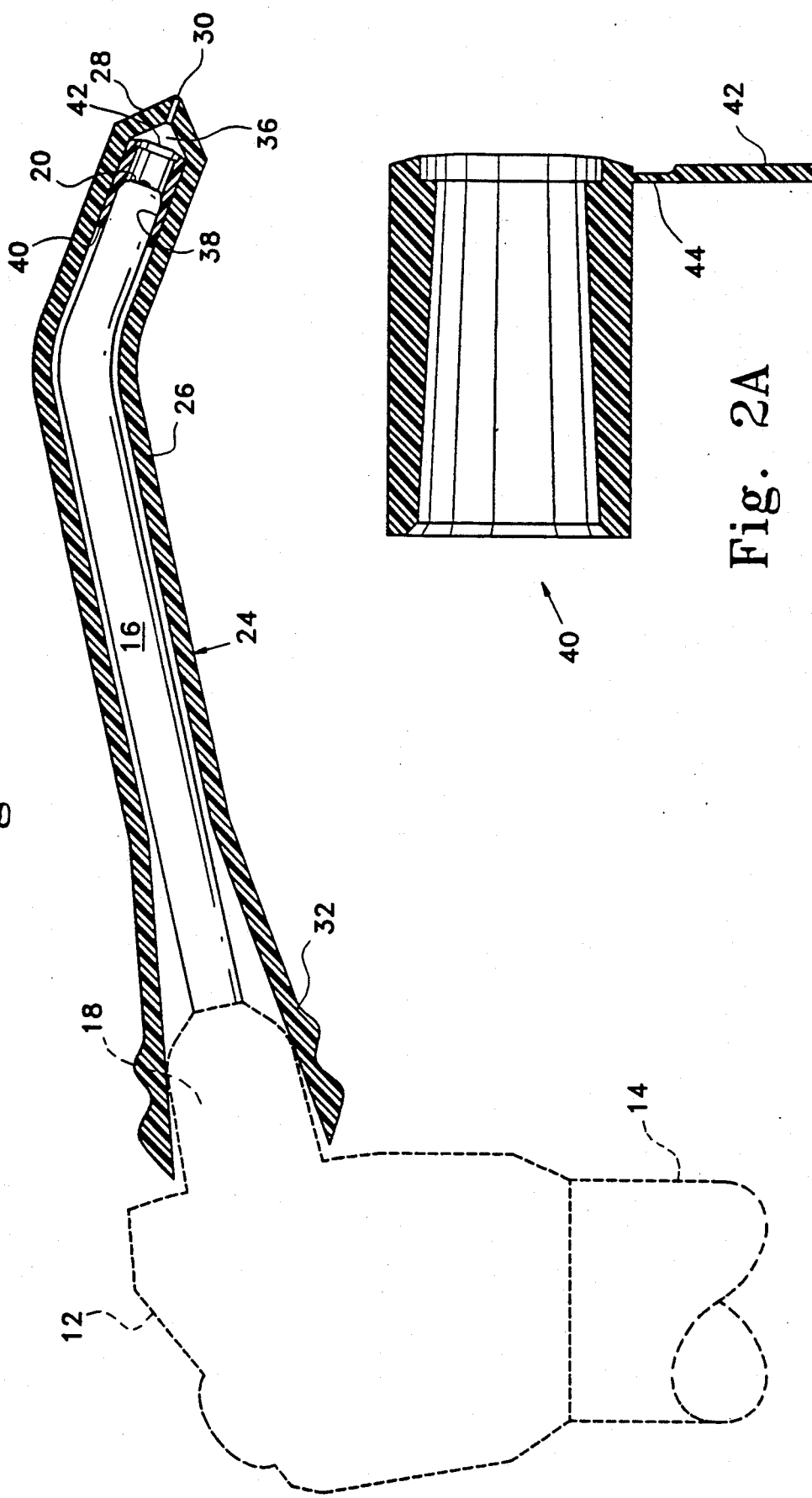
FIG. 2 is a side elevation view in section, showing a dental syringe cover or sheath positioned over a dental syringe. In the embodiment of FIG. 2 the syringe cover includes an enlarged bell-like base end, serving as a gripping and turning knob.

In the drawings, FIGS. 1 and 2 show a dental syringe generally identified as 10, including a head or base 12, a handle 14 and a nozzle or beak 16 comprising generally a cylindrical shaft with an angled end 17. At the base end of the syringe nozzle or beak 16, connecting the nozzle to the base or head 12 of the syringe, is a nut 18, which may be a multi-faceted nut for engagement by a wrench or a nut simply having a knurled or otherwise roughened cylindrical exterior surface. However, the principles of the invention are applicable to syringe heads which have a nut-free connection to the beak.

The dental syringe is typically used for flushing a dental patient's mouth during dentistry, and has openings at its tip end 20 for delivering water under pressure, compressed air, or a mixture of both. The dentist ordinarily controls the selection of air and/or water via a pair of buttons 22 on the head of the syringe device.

Figure 3:
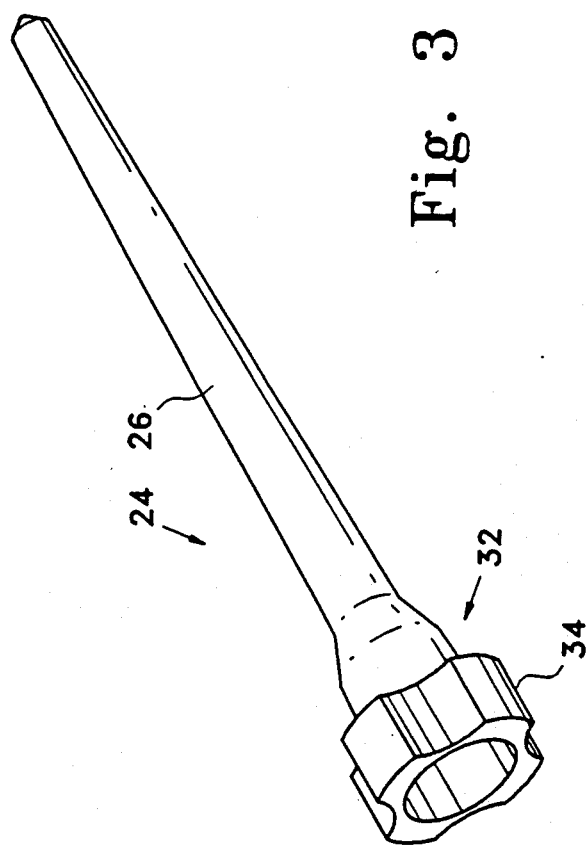
FIG. 3 is a perspective view showing a syringe cover such as in FIGS. 1 and 2.

In accordance with this invention, a dental syringe cover 24, preferably disposable (but optionally sterilizable) and of an injection molded plastic material such as polypropylene (or polyethylene), fits over the syringe nozzle 16 and also covers or partially covers the nut 18. The embodiment of the syringe cover 24 shown in FIG. 1 has a shaft portion 26 which is generally cylindrical, i.e. cylindrical or slightly tapered toward a tapered tip end 28 with a nozzle opening or restricted orifice 30. At the other end of the shaft 26 is a generally bell-shaped end 32 which not only loosely covers the nut or fastener 18 of the dental syringe, but also acts in a preferred embodiment as a handle for gripping by the user as the syringe cover device is installed onto the dental syringe, and more importantly FIG. 3 shows the bell-shaped feature 32 in perspective, with a series of radially extending projections 34 on this bell-shaped end for convenient gripping and twisting by the user, in order to fit the syringe cover 24 snugly in place. However, in another embodiment of the device, the bell-shaped end may simply be an enlarged cylinder or truncated conical portion, without any multiple facets or radial projections; or it may be not bell-shaped but only slightly larger than the syringe beak, with or without projections 34.

As shown in FIGS. 1 and 2, the tip 20 of the dental syringe stops short of the tip 28 and nozzle 30 of the syringe cover, in the installed position. This forms a gap or cavity 36 which acts as a post-syringe chamber within which fluid from the syringe collects en route to being ejected from the syringe cover nozzle 30. As indicated, the syringe shaft 16 is tightly sealed against a surface 38 of the syringe cover, in the last one-half inch or so of the syringe shaft. This may be accomplished via a reduced diameter at the interior of the syringe cover, at the surface 38, and this reduced diameter is preferably slightly smaller than the outside diameter of the dental syringe shaft itself at the tip. This establishes an interference fit between the syringe and the syringe cover in this area, requiring the cover to be pushed over the syringe tip with a moderate amount of force and assuring that a tight, fluid-impervious seal is formed around the syringe shaft in this area. As mentioned earlier, this prevents any air or water from the syringe from being pushed back along the exterior surface of the syringe shaft 16 toward the nut 18.

Figure 2A:
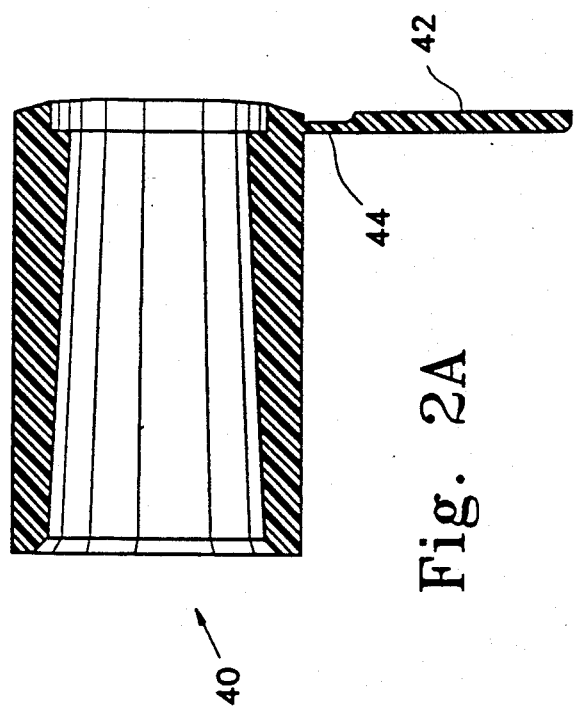
FIG. 2A is a view showing an internal mechanical check valve member, removed from the dental syringe cover of FIG. 2.

In the embodiment illustrated, the reduced diameter surface 38 of the syringe cover is formed by a small cylindrical insert 40 which may be used when a mechanical check valve is to be included in the syringe cover device. FIG. 2A shows the insert member 40, with a flap valve at its outer end comprising a flap 42 of plastic material connected to the cylindrical barrel portion by a plastic hinge 44. The cylindrical insert 40 fits tightly within the end of the syringe cover shaft or shank 26 and may be held there by press fitting.

The chamber or air gap 36 in the tip end 28 of the syringe cover has several advantages. One effect of this air gap is that in the delivery of water from the syringe, the gap 36 fills with water (and air, if air is also being delivered) and is then subject to the pressure delivered by the syringe itself, to deliver a well-directed stream of water through the syringe cover nozzle 30 at the extremity of the syringe cover. In contrast, if the syringe cover were configured such that the nozzle opening 30 were pressed closely against the syringe tip 20 itself (as shown, for example, in U. S. Pat. No. 4,907,968), the syringe cover opening 30 would interfere with the flowing stream of water by contacting the stream as it exited the syringe. Such an arrangement will not function well unless the opening in the syringe cover is made very large so as not to contact the water stream from the syringe; however, this will tend to defeat the purpose of the syringe cover by leaving the syringe tip exposed to contamination.

Another advantage afforded by the gap or chamber 36 of the present invention is that when compressed air and water are expelled together from the dental syringe, they are thoroughly mixed in the chamber 36, under pressure, and an aerated stream of the air/water mixture is delivered through the nozzle 30. This stream is more desirable in use than the stream which emanates from the uncovered dental syringe and which essentially is a stream of water having jets of air funneled toward it from peripheral openings in the syringe tip 20.

It is known that some retraction occurs within the syringe itself, after water is delivered from the syringe. This may be due to expansion and contraction of the flexible water line leading to the syringe, as well as other factors. This will cause a small part of the water contained in the chamber 36 to be pulled back into the syringe shaft 16 after use of the device for delivering water. This will not adversely affect the performance of the syringe covers of the invention.

Figure 4:
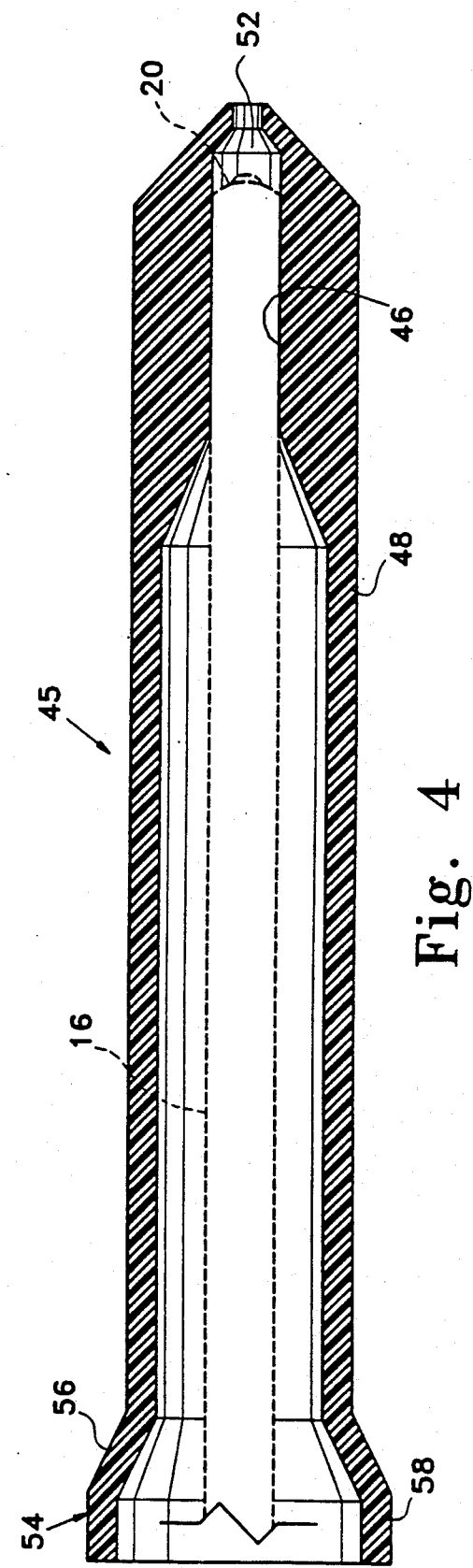
FIG. 4 is an elevational section view, showing a further embodiment of the invention.

FIG. 4 shows a somewhat modified form of syringe cover 45 in accordance with the invention. The cover 45 is shown in its underformed, straight configuration, with the syringe shaft 16 shown dashed inside—it actually has a bend as noted above. In this embodiment, the tip 20 of the syringe shaft 16, and the exterior of the shaft for a short distance behind this tip, engage against an integral reduced diameter portion 46 of the syringe cover, which again preferably is formed of polypropylene or similar material (it can comprise polyethylene No. 18BOA). The reduced diameter portion 46 comprises a thickening of the wall 48 of the syringe cover in this area, and the diameter (which may taper down toward the tip) is slightly smaller than the corresponding outside diameter of the syringe 16. This forms a fluid tight seal as discussed above.

The syringe cover 45 of FIG. 4 does not include any check valve in the form illustrated. Further, the syringe cover 45 is shown with a base end or nut end 54 which is again generally bell-shaped but which simply comprises a conical flare 56 and a final less steeply angled conical flare 58. Radial gripping projections can be included on this embodiment just as on the embodiment described above, if desired. However, FIG. 4 illustrates that the radial projections may in some cases be eliminated (on either the FIGS. 1-3 or FIG. 4 embodiment) and that the flared end 58 will still be grippable by the user although not as conveniently as with the gripping projections included. In other respects the syringe cover 45 is installed and operates similarly to what is described above, particularly in regard to the gap or chamber 52.

FIGS. 5 and 6 show another preferred form of the invention, wherein a dental syringe cover 60 is formed of natural rubber or of a rubbery synthetic material (e.g. silicone rubber), and includes a duckbill valve 62 at its delivery end. The duckbill valve 62 requires a somewhat rubbery, elastomeric material to be formed properly and to function properly. It acts as an absolute barrier to the intrusion of any contaminating fluids to the interior of the nozzle cover 60. In particular, this valve prevents retraction into the syringe.

The duckbill nozzle cover 60 may be formed by conventional injection molding techniques, with the duckbill valve itself formed as a slit 64 after molding, in a cutting operation. The valve opening 64 is a slit which remains entirely closed and in fact almost invisible to the eye in the absence of any internal pressure. When pressure is applied via the syringe tip 20 (shown in dashed lines), a gap or chamber 66 downstream of the syringe tip fills with fluid and forces the slit valve 64 open to form a nozzle having an opening size as defined by the flow rate of fluid. The gap or chamber 66 acts in much the same way as discussed above except that pressure in the chamber 66 is required before the duckbill slit valve/nozzle opens. Advantageous mixing of air and water, and aeration of the water, occur when compressed air and water are delivered together, as discussed above.

The duckbill valve embodiment 60 of the nozzle cover preferably is formed of natural rubber, particularly if it is to be disposable. If the cover is to be autoclavable, it is advantageously formed of silicone rubber. It has been found that the rubbery syringe cover can be advantageously injection molded from two materials which are essentially the same, but with different hardness. At the nut shield or cover end 70, and a portion of the shaft, the rubbery material preferably has a hardness in the range of 60 to 80 durometer; at the nozzle end 62, it can have a much softer characteristic of around 35 durometer, or a range of 30 to 40 durometer. This can be accomplished, in the injection molding process, by first inserting a premeasured ball of rubber with the softer characteristic into the female mold cavity, followed by a ball of rubber of the greater hardness. The two materials are essentially the same and are fully compatible, and the resulting injection molded product is significantly harder and more rigid at the nut shield end 70 than at the nozzle end. Thus, the user can more easily grip the nut shield end to insert it over the dental syringe, and more importantly, this provides for a firm grip of the cover on the shank of the dental syringe. A reduced internal diameter 72 of the syringe cover engages tightly and sealingly over the syringe shaft near its end.

FIG. 7 shows a dental syringe 80 having a disposable syringe tip or beak 82 in accordance with another embodiment of the invention. FIG. 8 shows the disposable tip 82 in cross section, fitting over a rigid air/water fitting 84 which is secured to the body of the syringe 80 by a nut 86, in the manner conventional syringe tips are held to the syringe body, permitting rotation. The air/water fitting 84 has an internal tube or conduit 88 for water, and a space or plenum 90 for air, delivered through air exit holes 92.

As explained above, one aspect of the present invention is that the air and water from a syringe can be mixed in a gap or space such as the elongated space 94 shown in the disposable syringe beak section 82. The air and water thus mixed inside the syringe cover form an improved spray or stream as compared to the typical spray from an uncovered dental syringe.

The disposable syringe section 82 snaps over and fits on the air/water fitting 84 in any suitable and convenient fashion. FIG. 8 shows an internal embossing 96 in the disposable cover, engageable with a circumferential groove 98 in the air/water fitting. In addition, an O-ring 100 may be included to seal against backflow leakage.

FIG. 9 shows another embodiment of a disposable syringe 110, comprising a disposable syringe section 112 and a preferably non-disposable air/water fitting 114. In this embodiment, the connection between the disposable syringe section 112 and the air/water fitting 114 is similar to that described above, but in this case the assembly avoids the need for a nut such as shown above. Instead, the air/water fitting 114 has a male threaded end 116 which fits directly into an internal thread typically included in a dental syringe head 118. The air/water fitting 114 thus replaces a conventional double-ended male threaded fitting which screws into the syringe head 118 and provides a male thread for receipt of the nut such as shown above. The nut provided a compression O-ring seal which permitted rotation of the syringe beak in a conventional syringe, but this rotation is afforded by the rotatable connection between the disposable beak section 112 and the air/water fitting 114 in the disposable syringe beak shown in FIG. 9.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

I claim:

1. A hygienic syringe cover for a rigid dental syringe used for delivering liquid and/or air into a patient's mouth, comprising:

a generally cylindrical shank of non-rigid material, having a liquid delivery end which tapers to a smaller diameter and an opposite, enlarged end of larger diameter, an enlarged portion at the opposite end with means for gripping the enlarged portion to install the syringe cover on a dental syringe and to rotate the syringe, a tip on the shank at said liquid delivery end, the tip including a flow restrictor orifice through which liquid and/or air is delivered from the dental syringe, and means associated with the shank for preventing backflow of liquids along the exterior surface of the dental syringe, between the dental syringe and the syringe cover.

2. The apparatus of claim 1, wherein said enlarged opposite end includes multifaceted handle means for providing a manual grip for installing the syringe cover, and for rotating the dental syringe with the cover.

3. The apparatus of claim 2, wherein the handle means comprises a series of radially extending projections for manual gripping by a user.

4. The apparatus of claim 1, wherein the means for preventing backflow comprises the shank being sized to engage its inner surface tightly over at least a portion of the exterior surface of the dental syringe.

5. The apparatus of claim 1, wherein the length of the shank of the syringe cover exceeds that of the dental syringe such that, when the syringe cover is installed, there is defined a gap of interior space between the tip of the dental syringe and the tip of the syringe cover at the end of the shank, the gap serving to retain liquid after use of the syringe.

6. The apparatus of claim 1, formed of a soft rubbery material at least at the tip of the syringe cover, and the tip having a one-way valve means comprising a flattened duckbill slit biased toward a closed position, serving as said flow restrictor orifice.

7. The apparatus of claim 6, wherein the syringe cover is formed integrally of a single piece of rubbery material, but with different hardness characteristics at the two ends, the opposite, enlarged end and a portion of the shank adjacent thereto being firmer and harder than the one way valve means at the tip, whereby the enlarged end and the shank portion are more rigid for gripping tightly against the exterior surface of the dental syringe when installed.

8. The apparatus of claim 7, wherein the soft rubbery material has a hardness durometer in the range of 30 to 40 at and near the tip, and a hardness durometer of about 60 to 80 at the opposite, enlarged end and in said shank portion adjacent thereto.

9. The apparatus of claim 6, wherein the soft rubbery material comprises silicone rubber.

10. A hygienic syringe cover for a rigid dental syringe used for delivering liquid and/or air into a patient's mouth, comprising:

a generally cylindrical shank of non-rigid material, having a liquid delivering end which tapers to a smaller diameter and an opposite, enlarged end of larger diameter, a tip on the shank at said liquid delivery end, the tip including a flow restrictor orifice through which liquid and/or air is delivered from the dental syringe, the length of the syringe cover exceeding that of the dental syringe such that, when the syringe cover is installed, there is defined a gap of interior space between the tip of the dental syringe and the tip of the syringe cover at the end of the shank, the gap serving to retain liquid after use of the syringe, and means associated with the shank of the syringe cover for preventing backflow of fluids along the exterior surface of the dental syringe, between the dental syringe and the syringe cover.

11. The apparatus of claim 10, wherein the means for preventing backflow comprises the shank being sized to engage its inner surface tightly over at least a portion of the exterior surface of the dental syringe.

12. The apparatus of claim 11, wherein the shank has an inside surface with a sharply reduced diameter for a short distance back from the tip, which engages tightly over the exterior surface of the dental syringe for preventing backflow.

13. The apparatus of claim 10, formed of a soft rubbery material at least at the tip of the syringe cover, and the tip having a one-way valve means comprising a flattened duckbill slit biased toward a closed position, serving as said flow restrictor orifice.

14. The apparatus of claim 13, wherein the syringe cover is formed integrally of a single piece of rubbery material, but with different hardness characteristics at the two ends, the opposite, enlarged end and a portion of the shank adjacent thereto being firmer and harder than the one way valve means of the tip, whereby the enlarged end and the shank portion are more rigid for gripping tightly against the exterior surface of the dental syringe when installed.

15. A disposable syringe tip or beak for a dental syringe having a syringe head having an internal thread in a recess through which pressurized air and water are provided, comprising:

a disposable beak section of plastic material, having a flow restricting orifice at a tip end through which air and/or water are delivered from the syringe, a rigid air/water fitting having a base end with a male thread for receipt in the internal thread of the syringe head, and having means for receiving pressurized air and water from the syringe head and for delivering air and/or water out a delivery end of the air/water fitting, and the air/water fitting and the disposable beak section having cooperating connection means for snap fitting a base end of the disposable beak section over the exterior surface of the air/water fitting outside the syringe head, to sealingly connect the disposable beak section to the air/water fitting.

16. The apparatus of claim 15, wherein the disposable beak section has a bend between its base end and its air/water delivery end, and wherein the connection means between the disposable beak section and the air/water fitting includes means permitting rotation of the disposable beak section, so as to change the orientation of the bend in the beak section.

17. A hygienic syringe cover for a rigid dental syringe used for delivering liquid and/or air into a patient's mouth, comprising:

a generally cylindrical shank of non-rigid material, having a liquid delivery end which tapers to a smaller diameter and an opposite, enlarged end of larger diameter, an enlarged portion at the opposite end, a tip on the shank at said liquid delivery end, the tip including a flow restrictor orifice through which liquid and/or air is delivered from the dental syringe, and means associated with the shank for preventing backflow of liquids along the exterior surface of the dental syringe, between the dental syringe and the syringe cover.

18. The apparatus of claim 17, in combination with a rigid dental syringe having means for delivering liquid and/or air into a patient's mouth, and wherein the length of the shank of the syringe cover exceeds that of the dental syringe such that, when the syringe cover is installed on the dental syringe, there is defined a gap of interior space between the tip of the dental syringe and the tip of the syringe cover at the end of the shank, the gap serving to retain liquid after use of the syringe and serving to help deliver a liquid or air/liquid mixture through the flow restrictor orifice.

* * * * *